United States Patent [19]
Williams et al.

[11] Patent Number: 5,957,972
[45] Date of Patent: Sep. 28, 1999

[54] IMPLANTS POSSESSING A SURFACE OF ENDOTHELIAL CELLS GENETICALLY-MODIFIED TO INHIBIT INTIMAL THICKENING

[75] Inventors: Stuart K. Williams; Alison Stopeck, both of Tucson, Ariz.

[73] Assignee: Arizona Board of Regents on Behalf of the University of Arizona, Tucson, Ariz.

[21] Appl. No.: 08/787,902

[22] Filed: Jan. 23, 1997

Related U.S. Application Data

[63] Continuation-in-part of application No. 07/953,474, Sep. 29, 1992, Pat. No. 5,628,781
[60] Provisional application No. 60/010,616, Jan. 26, 1996.
[51] Int. Cl.⁶ ........................................... A61F 2/06
[52] U.S. Cl. ............................................. 623/1; 435/372
[58] Field of Search ............................... 623/1; 435/240, 435/241, 366, 372

[56] References Cited

U.S. PATENT DOCUMENTS

| | | | |
|---|---|---|---|
| 4,820,626 | 4/1989 | Williams et al. | 435/1 |
| 4,883,755 | 11/1989 | Carabasi et al. | 435/240.2 |
| 5,035,708 | 7/1991 | Alchas et al. | 623/1 |
| 5,096,705 | 3/1992 | Goeddel et al. | 424/85.5 |
| 5,131,907 | 7/1992 | WIlliams et al. | 600/36 |
| 5,194,373 | 3/1993 | Williams et al. | 435/34 |
| 5,208,019 | 5/1993 | Hansson et al. | 424/85.5 |
| 5,230,693 | 7/1993 | Williams et al. | 600/36 |
| 5,312,380 | 5/1994 | Alchas et al. | 604/310 |
| 5,336,615 | 8/1994 | Bell et al. | 435/240 |
| 5,372,945 | 12/1994 | Alchas et al. | 435/267 |
| 5,441,539 | 8/1995 | Alchas et al. | 623/66 |
| 5,674,722 | 10/1997 | Mulligan et al. | 623/1 |

OTHER PUBLICATIONS

Friesel et al, "Inhibition of Endothelial Cell Proliferation by Gamma–Interferon" J. Cell Biol. 104:689–96, Mar. 1987.
Berger, "Healing of Arterial Prostheses in Man: Its Incompleteness", supra.
Feldman et al., "Low Efficiency of Percutaneous Adenovirus–Mediated Arterial Gene Transfer in the Atherosclerotic Rabbit", *J Clin Invest* 1995;95:2662–71.
Fishman, "Endothelium" A Distributed Organ of Diverse Capabilities, *Annl of NY Acad of Sci* 1982:1–8.
Glasberg et al., "Cultured Endothelial Cells Derived From Human Iliac Arteries", *In Vitro* 1982;18:859–66.
Graham et al., "Cultured Autogenous Endothelial Cell Seeding of Vascular Prosthetic Grafts", *Surg Forum* 1979;30:204–6.
Graham et al., "Expanded Polytetrafluorethylene Vascular Prostheses Seeded with Enzymatically Derived and Cultured Canine Endothelial Cells", *Surgery* 1982;91:550–9.
Hansson et al., "Interferon–γ Inhibits Arterial Stenosis After Injury", *Circ* 1991;84:1266–1272.
Hansson et al., "Interferon–γ Regulates Vascular Smooth Muscle Cell Proliferation and Ia Expression in Vivo and In Vitro", *Circ Res* 1988;63:712–719.
Herring et al., "A Single and Staged Technique for Seeding Vascular Grafts with Autogenous Endothelium", *Surgery* 1978;84:498–504.
Jaffe et al., "Culture of Human Endothelial Cells Derived From Umbilical Veins", *J Clin Invest* 1973;52:2745–56.
Jaffe et al., "Synthesis of Antihemophilia Factor Antigen by Cultured Human Endothelial Cells", *J Clin Invest* 1973;55:2757–64.
Jarrell et al, "Human Adult Endothelial Cell Growth in Culture", *J. Vasc. Surg* 1984;1:757–765.
Lewis, "Endothelium in Tissue Culture", *Am J Anat* 1922;30:39–59; and Jaffe et al., "Culture of Human Endothelial Cells Derived From Umbilical Veins", *J Clin Invest* 1973;52:2745–56.
Mann et al., "Construction of a Retrovirus Packaging Mutant and Its Use to Produce Helper–Free Defective Retrovirus," *Cell* 1983;33:153–159.
Sauvage et al., "Interspecies Healing of Porous Arterial Prostheses", *Arch Surg* 1974;109:698–705.
Simon et al., "Adenovirus–Mediated Gene Transfer of the CFTR Gene to Lungs of Nonhuman Primates: Toxicity Study", *Hum Gen Ther* 1993;4:771–80.
Von der Leyen et al., "Gene Therapy Inhibiting Neointimal Vascular Lesion: In vivo Transfer of Endothelial Cell Nitric Oxide Synthase Gene", *Proc Natl Acad Sci USA* 1995;92:1137–47.
Watkins et al., "Adult Human Saphenous Vein Endothelial Cells: Assessment of Their Reproductive Capacity for Use in Endothelial Seeding of Vascular Prostheses", *J Surg Res* 1984;36:588–96.
Wilson et al., "Implantation of Vascular Grafts Lined with Genetically Modified Endothelial Cells", *Science* 1989;244:1344–1346.
Williams, "Endothelial Cell Transplantation", *Cell Trans.* 1995;4:401–409.
Wu et al., "Restoration of Prostacyclin Synthesis by Transfer of PGHS cDNA", *Adv Prostagl Thrombox Leukotri* 1994;23:377–80.
Wu et al., "Role of Endothelium in Thrombosis and Hemostasis", *Annu Rev Med* 1996;47:315–31.

*Primary Examiner*—Robert A. Clarke
*Attorney, Agent, or Firm*—Antonio R. Durando

[57] ABSTRACT

Autologous and synthetic vascular implants that possess an external monolayer of endothelial cells genetically modified to express at least one of a number of therapeutic agents useful for the inhibition of smooth muscle cell proliferation are provided. In the preferred embodiment of this invention, the endothelial cells coating the implant are genetically-modified to express and secrete the protein interferon-gamma. The use of such an implant in vascular and heart surgeries would substantially increase both the patency of the graft and the rate of surgical success by inhibiting the expansive growth of the vessel or heart lumen in response to surgical damage, which is a major cause of graft failure.

9 Claims, 4 Drawing Sheets

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear    (xi) SEQUENCE DESCRIPTION: SEQ ID NO: 1:

GGCTTTTCAG CTCTGCAT                                                 18

(2) INFORMATION FOR SEQ ID NO: 2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear    (xi) SEQUENCE DESCRIPTION: SEQ ID NO: 2:

GGATGCTCTT CGACCTCG                                                 18

(2) INFORMATION FOR SEQ ID NO: 3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (xi) SEQUENCE DESCRIPTION: SEQ ID NO: 3:

TGAAGGTCGG AGTCAACGGA TTTGGT                        26

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (xi) SEQUENCE DESCRIPTION: SEQ ID NO: 4:

CATGTGGGCC ATGAGGTCCA CCAC                          24

(2) INFORMATION FOR SEQ ID NO: 5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear     (xi) SEQUENCE DESCRIPTION: SEQ ID NO: 5:

AGAAGTCCAG GTGAAGGTTA GAGGAGCAT                   29

(2) INFORMATION FOR SEQ ID NO: 6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear     (xi) SEQUENCE DESCRIPTION: SEQ ID NO: 6:

CTGCTTCACC GAGTGCTACA ATACTTGCT                   29

(2) INFORMATION FOR SEQ ID NO: 7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear     (xi) SEQUENCE DESCRIPTION: SEQ ID NO: 7:

CTGTCCAGGT GAGAAAGATC GAGATTGTGC GG                32

(2) INFORMATION FOR SEQ ID NO: 8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear     (xi) SEQUENCE DESCRIPTION: SEQ ID NO: 8:

GCCGTCTTGT CATGCGTGTG CTTGAATTTC CG                32

IMPLANTS POSSESSING A SURFACE OF ENDOTHELIAL CELLS GENETICALLY-MODIFIED TO INHIBIT INTIMAL THICKENING

RELATED APPLICATIONS

This application is a continuation-in-part of U.S. Ser. No. 07/953,474, filed on Sep. 29, 1992, issued as U.S. Pat. No. 5,628,781 on May 13, 1997, and is based on U.S. Provisional Application No. 60/010,616, filed Jan. 26, 1996.

BACKGROUND OF THE INVENTION

1. Field of the Invention

This invention pertains to the general field of vascular and heart surgeries. In particular, it provides autologous and synthetic vascular and heart implants that possess an internal monolayer of endothelial cells genetically modified to express at least one of a number of therapeutic agents useful for the inhibition of intimal thickening.

2. Description of the Prior Art

Angioplasty and reconstructive vascular surgery are routinely-utilized surgical procedures for the treatment of arteriosclerosis, such as atherosclerosis and medial arteriosclerosis, heart and renal failure, arterial aneurysms, and other conditions that require general vascular bypass to restore blood flow to areas of ischemia. These techniques normally involve injury to a portion of an artery or vein followed by implantation of a donor or synthetic vascular graft, stent, or other implant in order to replace or repair the injured vascular or heart portion. The term "graft" is well understood by those skilled in the art and refers to unattached tissue or material, whether synthetic or naturally occurring, that is implanted, or intended to be implanted, into the body. Additionally, the term "stent" is well understood by those skilled in the art and refers to a prosthesis lying or intended to lie within tubular structures in the body in order to provide support to that tubular structure. As utilized herein, the term "implant" is meant to include, but not to be limited to, all intravascular devices, whether autologous or synthetic, vascular prostheses, artificial hearts, heart valves, vascular stents, and vascular grafts. As utilized herein, the term "vascular" is meant to refer collectively to all tissues, or synthetic materials replacing or intending to replace such tissues, that directly contact flowing blood from veins and arteries and that possess an endothelium, such as, for example, blood vessels and heart tissues. Though the vascular grafting techniques discussed above are commonly utilized, they possess an alarmingly high rate of complication (between 30–50%).

There exist two principal causes of vascular graft failure: thrombosis and smooth muscle cell proliferation.

Thrombosis

The first principal cause of vascular graft failure is the development of blood clots (thrombosis) at the site of vascular injury, which constrict or close the arterial passageway, known in the art as the vascular lumen, and lead to decreased blood flow (ischemia) to tissues and organs. The reaction that leads to the clotting of certain blood cells, which are known as platelets, is catalyzed by a protein complex named thrombin, which forms in the blood in response to various stimuli. Thrombin is a multifunctional protease that induces platelet aggregation and stimulation and the activation of coagulation-stimulating factors, both of which lead to thrombosis. Paradoxically, thrombin also possesses antithrombotic properties, which depend almost entirely upon interactions with healthy endothelial cells. Endothelial cells are specialized cells that form the innermost cellular wall of veins and arteries, which is referred to in the art as the endothelium, as well as forming the inner lining of the heart. The normal role of healthy endothelial cells is to provide a thromboresistant and actively anti-thrombogenic surface that inhibits the formation of clots and the prothrombotic function of thrombin and that does not allow platelets or other blood cells to adhere to the walls of the endothelium. Endothelial cells accomplish this anti-thrombotic role in part by the synthesis of physiological factors, such as prostacyclin, nitric oxide, ecto-adenosine diphosphatase, tissue-plasminogen activator inhibitor-1, thrombo-modulin, protein S, and heparan sulfate proteoglycan. The antithrombotic action of several of these factors are either thrombin-mediated or thrombin-activated, and thus a substantial portion of the anti-thrombogenic function of endotheilial cells requires direct interaction with thrombin. Additionally, endothelial cells also block the actions of pro-coagulant and prothrombotic molecules produced in the subendothelial matrix. Some additional biological factors produced by or interacting with endothelial cells that affect thrombogenecity include: plasminogen activator, soluble CD-4, Factor VIII, Factor IX, von Wildebrand Factor, urokinase, interferons, tumor necrosis factor, interleukins, hematopoietic growth factor, antibodies, glucocerebrosidase, ADA, phenylalanine, hydroxylase, human growth hormone, insulin, and erythropoietin. As utilized herein, the term "therapeutic agents" is meant to refer collectively to all of the above-listed physiological agents and biological factors. Thus, endothelial cells provide a vast array of mechanisms that inhibit thrombus formation, and the loss of endothelial cell function, such as that loss resulting from cellular damage caused by vascular surgery, causes a marked shift in the homeostatic balance toward thrombosis. Indeed, all angioplastic surgeries cause removal of or significant damage to the endothelial cell lining of the target blood vessel and, thereby, this surgical procedure results in a blood contacting surface that is extremely thrombogenic.

To overcome this first principal cause of vascular graft failure, researchers have attempted to create vascular grafts with a surface that is thromboresistant, with the majority of these efforts directed toward an improved polymer surface. Perhaps the ideal blood-surface interface is the naturally occurring human endothelium. If present on a prosthetic graft, it would offer many of the advantages of a native vessel. Unfortunately, endothelialization occurs spontaneously only to a limited degree in prosthetic grafts when placed into humans.

Seeding endothelial cells onto preclotted prosthetic grafts prior to implantation has accelerated the formation of an endothelial cell coverage of grafts in animals, but this technique has had limited use in humans. For a thorough listing of such experiments, see U.S. Pat. No. 5,131,907, entitled "Method of Treating a synthetic Naturally Occurring Surface with a Collagen Laminate to Support Microvascular Endothelial Cell Growth, and the Surface Itself," which is incorporated by reference herein in its entirety.

Endothelial cells from animal sources have been studied in culture since the 1920's. In 1973, Jaffe et al. successfully cultured endothelial cells from human umbilical veins, and these cells have been characterized functionally. See Jaffe et al., "Synthesis of Antihemophilia Factor Antigen by Cultured Human Endothelial Cells", *J Clin Invest* 1973;55:2757–64; Lewis, "Endothelium in Tissue Culture", *Am J Anat* 1922;30:39–59; and Jaffe et al., "Culture of Human Endothelial Cells Derived From Umbilical Veins", *J Clin Invest* 1973;52:2745–56. These cell cultures demonstrate a very limited growth potential, but the total number of cells produced from a single umbilical vein is usually quite limited, in the range of a 10–100-fold increase in harvested endothelial cells.

While several techniques have been proposed to increase the number of cells produced by the use of human umbilical vein endothelial cells, the ability to culture endothelial cells in large number remains less than ideal. Investigators have had limited success in culturing human and adult endothelial cells from pulmonary arteries and veins, but only for short periods of time. It has also been shown that human iliac artery endothelial cells may be cultured for a short number of passages. In a study by Glasberg et al., for example, it is reported that 50 to 500 viable cells can be obtained per 5-inch vessel segment, a very low yield. "Cultured Endothelial Cells Derived From Human Iliac Arteries", *In Vitro* 1982;18:859–66. Fry et al. have also reported successfully culturing human adult endothelial cells from abdominal arteries removed at the time of cadaver donor nephrectomy, but these cells also demonstrated limited proliferative capacity.

It is apparent from existing techniques that it is difficult to produce enough cells to preendothelialize a graft with a reasonable amount of vessel from the donor patient. Rather than completely endothelializing a graft prior to implantation, the concept of subconfluent "seeding" of a preclotted graft developed. Seeding vascular grafts with autogenous endothelial cells has recently been shown to increase the rate of endothelial coverage of the grafts of experimental animals. Herring et al., "A Single and Staged Technique for Seeding Vascular Grafts with Autogenous Endothelium", *Surgery* 1978;84:498–504; Graham et al., "Cultured Autogenous Endothelial Cell Seeding of Vascular Prosthetic Grafts", *Surg Forum* 1979;30:204–6; Graham et al., "Expanded Polytetrafluoroethylene Vascular Prostheses Seeded with Enzymatically Derived and Cultured Canine Endothelial Cells", *Surgery* 1982;91:550–9. Once covered by endothelium, grafts in dogs have been shown to be less thrombogenic as measured by platelet re-activity, to be more resistant to inoculation from blood-borne bacterial challenge, and to have prolonged patency of small-caliber vascular grafts. For a thorough listing of such experiments, see U.S. Pat. No. 5,131,907, supra.

A point of major concern when translating to human graft seeding has been the ability to produce enough endothelial cells with the use of human vascular tissue to allow seeding at a density high enough to attain endothelial cell coverage of the graft. Watkins et al., using human saphenous vein remnants following coronary artery bypass surgery, were able to produce small quantities of endothelial cells in culture and report a low-fold increase in confluent cell area obtained in culture after 4–6 weeks. Watkins et al., "Adult Human Saphenous Vein Endothelial Cells: Assessment of Their Reproductive Capacity for Use in Endothelial Seeding of Vascular Prostheses", *J Surg Res* 1984;36:588–96.

Even if it were possible to substantially expand the number of endothelial cells available through vigorous culturing techniques, concerns would still remain concerning the "health" of these endothelial cells after as many as 40 or 50 population doublings. Furthermore, the incubation of such cells in cultures that are foreign to their natural environment raises further concerns about genetic alterations and/or patient contamination with viruses, toxins, or other damaging materials.

Many endothelialization procedures are suggested in the literature. Investigations in this area have been complicated by the diverse nature of the endothelium itself and by the species to species differences that have been found relating to the behavior and characteristics of the endothelium. Fishman, "Endothelium A Distributed Organ of Diverse Capabilities", *Annl of NY Acad of Sci* 1982:1–8; Sauvage et al., "Interspecies Healing of Porous Arterial Prostheses", *Arch Surg* 1974;109:698–705; and Berger, "Healing of Arterial Prostheses in Man: Its Incompleteness", supra. Nonetheless, the literature is replete with reports of experiments involving the seeding of endothelial cells on various grafts, in various species, with a mixture of results. For a thorough listing of such experiments, see U.S. Pat. No. 5,131,907, supra.

It has been previously recognized that human microvascular endothelial cells, that is, the cells which are derived from capillaries, arterioles, and venules, will function suitably in place of large vessel cells even though there are morphological and functional differences between large vessel cells and microvascular endothelial cells in their native tissues.

U.S. Pat. No. 5,131,907, supra, describes the treatment to confluence of a vascular graft or other implant using microvascular endothelial cells that are separated from fat that is obtained at the beginning of an uninterrupted surgical procedure: in brief, fat tissue is removed from the patient after sterile conditions have been established, microvascular endothelial cells in that fat are then quickly separated from their related tissue by enzymatic digestion and centrifugation, and the cells are deposited on a surface by gravity or by filtration, which surface is then implanted into the patient during the latter stages of the same operation. A second uninterrupted surgical procedure for the creation of such vascular grafts that utilizes a crude fat slurry is also described: in brief, fat tissue is removed from the patient after sterile conditions have been established, the fat is homogenized to form a cellular slurry, this slurry is applied to an implant, and then this implant is implanted into the patient during the latter stages of the same operation. The synthetic vascular graft created by this protocol possesses a seeded monolayer of endothelial cells that is sufficient to promote spontaneous confluent endothelialization in vivo after implantation. This endothelialized graft is sufficiently thromboresistant to inhibit thrombosis, and, therefore, the use of this type of endothelialized graft substantially increases both graft patency and the surgical success rate of vascular grafting.

Additionally, U.S. Pat. No. 5,628,781, which is entitled "Improved Implant Materials, Methods of Treating the Surface of Implants with Microvascular Endothelial Cells, and the Treated Implants Themselves," describes a method for the creation of improved endothelialized vascular implants possessing substantially-enhanced anti-thrombogenic properties. First, the method describes the creation of a synthetic vascular graft possessing a monolayer of endothelial cells genetically modified to express any of a wide range of therapeutic agents. This enhanced expression of therapeutic agents, comprising the anti-thrombogenic proteins described hereinabove, would substantially improve graft patency and reduce localized thrombosis. Second, this method describes the use of improved polymers for the enhancement of graft anti-thrombosis. It has been observed that endothelial cells exhibit reduced thrombogenicity when in contact with different matrix proteins of the basement membrane as compared to tissue collagen. Implant materials can be treated by glow-discharge plasma modification to produce a surface rich in amines that possesses properties similar to those of the basement membrane. Thus this modified material induces these improved anti-thrombotic properties of endothelial cells normally stimulated by the basement membrane.

Additionally, some of the present inventors have engaged in substantial prior research work relating to the field of this invention, with numerous scientific publications and U.S. and foreign patents. The U.S. patents included in this work comprise: U.S. Pat. No. 4,820,626, U.S. Pat. No. 4,883,755, U.S. Pat. No. 5,035,708, U.S. Pat. No. 5,194,373, U.S. Pat. No. 5,230,693, U.S. Pat. No. 5,312,380, U.S. Pat. No. 5,372,945, and U.S. Pat. No. 5,441,539. The scientific publications included in this work comprise: Williams, "Endothelial Cell Transplantation", *Cell Trans.* 1995;4:401–409; and Wilson et al., "Implantation of Vascular Grafts Lined with Genetically Modified Endothelial Cells", *Science* 1989;244:1344– 1346. These publications and patents provide further insight into and background for the present invention as well as additional methodological direction and description, and, thus, these publications and patents are incorporated by reference herein in their entirety.

In an improvement to this technique of Williams et al., U.S. Pat. No. 5,336,615 describes the genetic modification of endothelial cells with an additional gene, specifically the c-src gene, which increases the migrative ability of endothelial cells, and the subsequent vascular transplantation of these modified cells, whether directly or as a monolayer coating on a synthetic vascular graft, in order to increase endothelial cell migration onto the graft and to decrease thrombus formation. This patent provides an additional overview of many of the background procedures relating to the present invention and is therefore incorporated herein in its entirety.

Intimal Thickening

The second principal cause of vascular graft failure is the development of vascular stenosis, the narrowing of the arterial or venous lumen, due to expansive growth of the innermost cellular layer of a blood vessel, such growth known in the art as intimal thickening (generic) or intimal hyperplasia, in response vascular damage. As part of the inflammatory and reparative response to vascular damage, such as that resultant from vascular surgeries, inflammatory cells, including monocytes, macrophages, and activated polymorphonuclear leukocytes and lymphocytes, often form inflammatory lesions in the blood vessel wall. This formation induces activation of cells in the intimal and medial cellular layers of the blood vessel or heart. This activation may include the migration of cells to the innermost cellular layers, known as the intima. Such migrations pose a problem for the long-term success of vascular grafts because endothelial cells release smooth muscle cell growth factors, such as platelet-derived growth factor, interleukin-1, tumor necrosis factor, transforming growth factor-beta, and basic fibroblast growth factor, that cause these newly-migrated smooth muscle cells to proliferate. Additionally, thrombin has been demonstrated to promote smooth muscle cell proliferation both by acting as a growth factor itself and by enhancing the release of several other growth factors produced by platelets and endothelial cells. Wu et al., "Role of Endothelium in Thrombosis and Hemostasis", *Annu Rev Med* 1996;47:315–31. This proliferation causes irregular and uncontrolled growth of the intima into the lumen of the blood vessel or heart, which constricts and often closes the vascular passage. As utilized hereinafter, the term "intimal hyperplasia" is meant to refer specifically to the proliferation of smooth muscle cells present in the intima. Often, irregular calcium deposits in the media or lipid deposits in the intima accompany these growths, such lipid deposits normally existing in the form of cholesterol and cholestryl esters accumulated within macrophages, T lymphocytes, and smooth muscle cells, and these calcium and lipid deposits cause arteriosclerotic hardening of the arteries and veins and eventual vascular failure. These arteriosclerotic lesions caused by vascular grafting can also be removed by additional reconstructive vascular surgery, but the failure rate of this approach due to restenosis has been observed to be between thirty and fifty percent.

Because such surgical therapies have proven unsuccessful, many pharmacological treatments have been proposed for the treatment of vascular stenosis, though these treatments have met with limited success. One such proposed treatment has focused on the use of the secretory T lymphocyte protein interferon-gamma ($\gamma$-IFN), which has been demonstrated to be a potent inhibitor of smooth muscle cell proliferation. The isolation and characterization of $\gamma$-IFN is described in detail in U.S. Pat. No. 5,096,705, which is incorporated by reference herein in its entirety. Parenteral administration of $\gamma$-IFN has been suggested as a potential treatment for vascular stenosis. Recombinant $\gamma$-IFN was demonstrated by Hansson et al. to inhibit the proliferation of exponentially replicating smooth muscle cells in vitro, and a dose-dependent relationship was found to exist between $\gamma$-IFN dose and inhibition of cell proliferation. Hansson et al., "Interferon-$\gamma$ Regulates Vascular Smooth Muscle Cell Proliferation and Ia Expression In Vivo and In Vitro", *Circ Res* 1988;63:712–719. Additional evidence obtained in this investigation suggested that $\gamma$-IFN acts by blocking the transition from $G_0$ to $G_1$ or an early event during the $G_1$ phase of the cell cycle in vascular smooth muscle cells. It was also observed that low levels of $\gamma$-IFN are secreted locally within the intima by activated T lymphocytes during the normal vascular response to injury, and thus the production of $\gamma$-IFN may be a part of the natural cellular immune and reparative response to vascular lesions. Hansson et al., supra. In subsequent work, Hansson et al. have demonstrated that parenteral administration of recombinant $\gamma$-IFN in a murine model reduced the size of intimal lesions by as much as fifty percent. Hansson et al., "Interferon-$\gamma$ Inhibits Arterial Stenosis After Injury", *Circ* 1991;84:1266–1272. In this study, a marked reduction in the growth rate of smooth muscle cells within vascular lesions was only observed during the first two weeks of $\gamma$-IFN administration, suggesting that the ultimate reduction in vascular lesion size may be due to this initial inhibition of cellular proliferation. However, complete inhibition of intimal hyperplasia and subsequent vascular failure was not achieved. Hansson et al. have received a U.S. Pat., No. 5,208,019, relating to this work. Thus, though administration of recombinant $\gamma$-IFN has significant potential as a treatment for smooth muscle cell proliferation during vascular stenosis, no currently viable method for that treatment exists. Other pharmacological therapies, such as the administration of heparin, calcium channel blockers, and angiotensin antagonists, have been proposed and tested, and these therapies have also proven inadequate to inhibit intimal hyperplasia secondary to vascular surgery.

Because these surgical and pharmacological therapies for the control of smooth muscle cell proliferation and intimal hyperplasia have to date been unsuccessful in human clinical trials, genetic modification of endothelial cells has been proposed as a novel method for the targeted inhibition of vascular stenosis and treatment of arteriosclerosis. Hansson et al. and Wu et al., supra. Gene therapy offers several advantages in the inhibition of smooth muscle cell growth and intimal hyperplasia by directly affecting the microenvironment of the blood vessel. Recombinant gene expression may provide a more-nearly physiological production of target factors and would alleviate the need for repeated infusions of large quantities of an exogenous preparation of such factors, which could cause considerable side effects. A number of transformation vectors and protocols have been predicted to be potentially useful in the transfer of gene constructs into endothelial cells, including, but not limited to, the following: (i) viral vectors, such as adenovirus, retroviruses, and adeno-associated viruses, (ii) non-viral vectors, such as cationic lipids and targeted polylysine-DNA condensation, (iii) electrophoretic methods, (iv) calcium-phosphate techniques, and (v) metaloprojectile transformation methods utilizing tungsten, gold, or other such suitable metals.

Other vectors having characteristics useful in the transformation of endothelial cells will be apparent to those skilled in the art. The term "vector" is well understood in the art and refers to any vehicle for the transformation of a cell or organism. Additionally, the term "transformation" is well understood in the art and refers to the addition of genetic material into a cell or organism, such "genetic material" understood by those skilled in the art to consist of "genes" or parts thereof, which are DNA or RNA sequences, whether synthetic or naturally occurring, that encode a functional protein or RNA molecule. Proposals for the use of gene therapy normally involve the transformation of endothelial cells in vivo with adenovirus and lipofectin-Sendai viruses and have been successfully accomplished for the transformation of prostaglandin H synthase-1 and nitric oxide synthase-III (NOS-III). Wu et al., "Restoration of Prostacyclin Synthesis by Transfer of PGHS cDNA", *Adv Prostagl Thrombox Leukotri* 1994;23:377–80 and Von der Leyen et al., "Gene Therapy Inhibiting Neointimal Vascular Lesion: In Vivo Transfer of Endothelial Cell Nitric Oxide Synthase Gene", *Proc Natl Acad Sci USA* 1995;92:1137–47. The NOS-III transformation study by Von Der Leyen et al. utilizing a murine model is the only study to date that has documented any therapeutic effects with in vivo gene transfer, though the in vivo method presented in this study was unable to completely inhibit intimal hyperplasia. Additionally, in vivo protocols for the treatment of pre-existing arteriosclerotic lesions would be further hampered by the fact that viral transformation efficiency is markedly reduced when transforming arteriosclerotic blood vessels as compared to those without lesions. Feldman et al., "Low Efficiency of Percutaneous Adenovirus-Mediated Arterial Gene Transfer in the Atherosclerotic Rabbit", *J Clin Invest* 1995,95:2662–71. This is a significant problem for in vivo methodologies, because high titers of these vectors have been demonstrated to elicit immunologic reactions and vascular inflammatations. Simon et al., "Adenovirus-Mediated Gene Transfer of the CFTR Gene to Lungs of Nonhuman Primates: Toxicity Study", *Hum Gene Ther* 1993;4:771–80. With the existence of these significant limitations, such in vivo methodologies for the treatment of vascular stenosis are currently unfeasible.

Thus, there exists a need for a medical treatment for vascular, heart, and renal failures that inhibits both thrombogenicity and smooth muscle cell proliferation secondary to surgery.

SUMMARY OF THE INVENTION

The present invention discloses a new method for the prevention of intimal thickening, as well as thrombosis, resultant from vascular damage caused by angioplasty and other vascular surgeries. This is achieved by the coating of an implant with endothelial cells genetically modified to express a medicinal agent, such as, for example, recombinant γ-IFN, that is useful for the prevention of smooth muscle cell proliferation prior to implantation of the implant. This improvement in surgical methodology is particularly important because there currently exists no effective treatment for surgical graft failure due to smooth muscle cell proliferation.

A second objective of this invention is to provide a treatment for atherosclerosis and similar vascular diseases.

A third objective of this invention is to provide a stable and reliable method for the chronic, parenteral administration of any protein or protein-derived factor.

Therefore, to achieve these objectives, the present invention is a method for the creation of an implant possessing a layer of endothelial cells genetically-modified to express a medicinal agent useful for the prevention of smooth muscle cell proliferation and the subsequent implantation of this implant. The expression of such medicinal agents by a layer of endothelial cells coating an implanted vascular implant substantially decreases both thrombosis and intimal hyperplasia, and thereby significantly increases both the implant patency and the rate of surgical success.

It is also expected that this implant will be utilized as a treatment for arteriosclerosis. Removal of arteriosclerotic plaques and their subsequent replacement with implants modified by the method of the present invention will provide an anti-thrombogenic and anti-intimal-thickening environment that will inhibit and discourage the recurrence of the blood vessel narrowing.

Additionally, because the method of the current invention allows the stable and reliable implantation of genetically-modified endothelial cells into humans via an anti-thrombogenic and anti-intimal-thickening vascular implant, other recombinant genes are also expected to be added to the retroviral construct prior to transformation and the resultant endothelial cells implanted into humans on vascular implants in order to obtain synthetic vascular implants that possess novel genetic properties useful for other medicinal therapies. Thereby, implantation of these novel medicinal implants would provide a parenteral route of introduction for any recombinant protein or protein product, allowing the consistent, chronic, parenteral administration of any soluble protein factor. Proteins that are normally not secreted outside the cell can be modified by well-established recombinant genetic techniques in order to cause the secretion of these proteins, and these recombinant techniques, such as, for example, the addition of an N-terminal cell signaling protein sequence to these proteins, are well known and understood by those skilled in the art.

Various other purposes and advantages of the invention will become clear from its description in the specification that follows and from the novel features particularly pointed out in the appended claims. Therefore, to the accomplishment of the objectives described above, this invention consists of the features hereinafter illustrated in the figures, fully described in the detailed description of the preferred embodiment and particularly pointed out in the claims. However, such figures and description disclose but one of the various ways in which the invention may be practiced.

BRIEF DESCRIPTION OF THE DRAWINGS

FIG. 1 is a bar graph-representation of data collected from conditioned media from control, _-gal transduced, and γ-IFN transduced human microvessel endothelial cells that was collected after 24 hours in culture and assayed for PDGF (from $5 \times 10^5$ cells) and γ-IFN (from $1 \times 10^5$ cells)

protein by ELISA. A * denotes statistical significance at P<0.05 compared to control nontransduced endothelial cells.

DETAILED DESCRIPTION OF THE PREFERRED EMBODIMENT

The substance of this invention lies in the recognition that endothelial cells present on implants can be genetically-modified to inhibit both thrombosis and smooth muscle cell-related intimal thickening, the result being an implant with improved patency and a decrease in the rate of failure of surgeries due to restenosis of such implants.

It should first be noted that any one of several different genetic alterations, as well as combinations thereof, to endothelial cells that are present on implants would inhibit thrombosis, intimal thickening, or both thrombosis and intimal thickening. However, the use of any one, or a combination of several, genetic modification that allows the inhibition of both of these causes of implant failure would be sufficient to allow the practice of the present invention. Therefore, the use by the inventors of one specific genetic modification or set of genetic modifications is not meant to be a limitation upon the present invention; rather, such use is meant to be illustrative of but one of the multiple methods in which the present invention can be practiced and is merely meant to represent the preferred embodiment thereof.

The preferred embodiment of the present invention comprises coating an implant with endothelial cells genetically modified to express γ-IFN and the subsequent implantation of this implant into the patient. As will become evident from the examples described below, the presence of endothelial cells expressing recombinant γ-IFN has been demonstrated to substantially inhibit smooth muscle cell proliferation. With the substantial inhibition of intimal hyperplasia resultant from γ-IFN expression by endothelial cells present on an implant, it has been found that the inhibition of thrombosis caused by the natural antithrombotic properties of the endothelial cell layer on the implant is sufficient to prevent implant failure due to intimal hyperplasia and thrombosis, and, though further modifications could increase the antithrombotic potential of these cells, no such additional modifications were necessary.

A synthetic or autologous implant can be coated with modified endothelial cells and then implanted into a patient by multiple methods by those skilled in the art. The preferred method of the inventors comprises:

1. Harvesting the Patient's Endothelial Cells. This can be accomplished by obtaining endothelial cell-rich tissues, such as fat tissue, and separating the endothelial cells from that tissue according to the methodology described in U.S. Pat. Nos. 5,035,708 and 5,312,380, supra. An additional methodology includes the selection of endothelial cells that can be implanted into the patient through the use of, for example, anti-rejection techniques or processes;

2. Transformation of the Patient's Endothelial Cells with γ-IFN. Inserting the γ-IFN gene or a part thereof, as well as any other recombinant genes of interest or parts thereof, into the harvested endothelial cells can be accomplished by utilizing, for example, a retroviral vector and, in particular, a retroviral packaging system that produces viral vector particles that are free of replicating virus, and then selecting for positive transformants utilizing, for example, and antibiotic selection protocol. Additional methods of genetic transformation, such as those listed supra, can also be employed successfully. See Mann et al., "Construction of a Retrovirus Packaging Mutant and Its Use to Produce Helper-Free Defective Retrovirus," *Cell* 1983;33 :153–159;

3. Coating an Implant with Transformed Cells. Application of the isolated, transformed, and selected endothelial cells onto an implant can be accomplished, for example, either (1) by adding a cellular suspension of these cells to the implant and then sealing the ends of that implant or (2) by layering these cells upon the surface of the implant, both performed according to the methodology described in U.S. Pat. No. 5,230,693, entitled "A Method of Treating a Synthetic or Naturally Occurring Surface with Microvascular endothelial Cells and the Treated Surface."

4. Implantation. Implanting the seeded implant can be accomplished using well known and described standard fine surgical techniques for vascular surgeries, interventional radiology, angioplasty, and organ-tissue transplantation.

These steps assume that the severity, location, and amenability of the disease to vascular bypass surgery with autologous, synthetic, or other implants was assessed prior to surgery by performing diagnostic catheterization of the patient. In any case, because the implants derived from the above-described method possess a layer of endothelial cells expressing the recombinant protein γ-IFN, these implants possess substantial antithrombotic and anti-intimal-hyperplasiatic properties that significantly increase both the implant patency and the rate of surgical success.

In some embodiments of the present invention, a gene expressing an additional therapeutic factor known to inhibit thrombosis, such as those therapeutic factors listed above, or intimal hyperplasia could be added to the vector construct and thereby be stabily integrated into and expressed by the transformed endothelial cells. These modifications would further reduce thrombus formation or smooth muscle cell proliferation. Such modifications of the vector can be accomplished by well known recombinant genetic methodologies that are apparent to those skilled in the art.

In other embodiments of the present invention, other recombinant genes could be added to the vector construct, the effect of such additions being the parenteral in vivo expression of such recombinant genes. This expression would allow the systemic administration of such recombinant genes via their secretion into the circulatory system. Such recombinant genes could include, for example, insulin, thyroid hormone, clotting factors, and alpha$_1$ anti-trypsin, or genes that protect normal endothelium from toxicity, limit leukocyte adhesion or invasion in inflammation, or destroy tumor vasculature as an anti-cancer therapy, to name but a few potential therapeutically-useful examples.

In a further embodiment, the present invention is meant to provide a therapy for arteriosclerosis. This therapy consists of the removal of a region of arteriosclerotic blood vessel, accomplished by standard, well-known fine surgical techniques, followed by the implantation of a vascular implant created by the method of the present invention that expresses γ-IFN or another medicinal agent that inhibits intimal hyperplasia; such a procedure both removes the region of the disease and creates a healthy vascular passage that, because of the anti-intimal-hyperplasiatic properties of the implant, is resistant to a recurrence to the disease.

U.S. Pat. No. 5,336,615, supra, describes the genetic of endothelial cells to express the c-src gene, which increases the migrative ability of endothelial cells, and the subsequent implantation of these cells into an animal on a vascular graft. This gene is a representative molecule of the src-family of membrane-bound tyrosine kinases, which is localized on the cytoplasmic, or intracellular, side of the plasma membrane. This protein exerts its effects solely inside the cell, and it is not secreted outside of the cell. Also, the use of this vascular graft is limited to implantation in animals. Thus, though this patent bears a prima facie resemblance to the third objective of the present invention, this patent is distinguished from that objective in that this patent did not anticipate a drug-delivery system utilizing a modified graft, but instead merely suggested a localized, intracellular improvement for the reendothelialization of synthetic vascular grafts.

Without intending to limit the scope of the present invention in any manner, the following examples are included in order to provide a more thorough description of the present invention.

EXAMPLE I

Transformation of Endothelial Cells With Recombinant γ-IFN

Human artery or venous endothelial cells were isolated and cultured by a modification of the methods of Jarrell et al., "Human Adult Endothelial Cell Growth in Culture", *J. Vasc. Surg* 1984;1:757–765. In brief, vessels were cleaned, removing the fat and connective tissue, and rinsed in serum-free medium. The luminal vessel surfaces were treated with 4 mg/ml collagenase (Boehringer Mannheim) and 4 mg/ml BSA (Sigma) for 30 minutes at 37° C. to allow detachment of endothelial cells from the lumen surface. Detached cells were collected by flushing the vessel lumen with 20–50 ml of medium (medium 199, 20% heat-inactivated fetal bovine serum, 5 mM HEPES (Sigma), 1.7 mM L-glutamine (Gibco BRL), and 60 βg/ml endothelial cell growth supplement (ECGF) containing 25 μg/ml heparin). Cells were pelleted, resuspended, and plated on polystyrene flasks (Corning) coated with 1% gelatin. Endothelial cell origin was determined by morphology and positive staining for Factor VIII-related antigen.

Following isolation of endothelial cells, the connective tissue and adventitia were removed from the vessel. The intima was minced and digested with collagenase and BSA for 5 hours at 37° C., with gentle agitation. The digestate was centrifuged at 700×g for 5 minutes, and the pellet was resuspended in medium before plating. After 3 days, the undigested minced tissue was removed, and fresh media added to the adherent cells. Smooth muscle cell origin of derived cells was confirmed by positive immunohistochemical staining for alpha smooth muscle cell actin.

Supernatants of high titer ($1 \times 10^6 – 1 \times 10^7$ cfu/ml) retrovirus containing the beta-galactosidase (β-gal) or γ-IFN genes were provided by Viagene, Inc., San Diego, Calif. The retroviral backbone was from the Moloney murine leukemia virus. Viral structural genes were replaced by either the *E. coli* β-gal or human γ-IFN genes. Media containing protamine sulfate at 750 μg/ml and retroviral supernatants containing either the β-gal or γ-IFN gene was added to endothelial cells seeded at 30–40% confluence one day after plating. Several different polycations, including polybrene, DEAE dextran, and protamine sulfate, were used over a concentration range. Protamine sulfate produced the highest transduction efficiencies at a concentration of 750 μg/ml. Endothelial cells were exposed to viral supernates for at least 4 hours. Endothelial cells were transduced twice at a multiplicity of infection (MOI) of 5. Exposing the cells twice to viral particles at an MOI of 5 produced higher transduction efficiencies than single transductions at an MOI of 10. Endothelial cells were then fixed in 2% formaldehyde and stained with an X-gal solution (5 mM Potassium Ferricyanide, 5 mM Potassium Ferrocyanide, 2 mM MgCl$_2$, and 1 mg/ml X-gal in PBS) at 37° C. for 24 hours. Transduction efficiency was calculated as the number of cells staining positive for β-gal divided by the total number of cells counted, and transduction efficiencies ranged from 25–35% prior to selection. Forty-eight hours after transduction, G418 (Geniticin; Gibco BRL) was added at 1000 μg/ml for microvessel endothelial cells and 400 μg/ml for iliac artery or vein endothelial cells until all mock-transduced cells were dead. Control endothelial cells were not exposed to viral supernatants or to G418 selection. Only G418 selected cells were used in experiments.

To determine whether transformed endothelial cells expressed γ-IFN and β-gal, γ-IFN and γ-gal proteins were measured from the conditioned media of control, β-gal, and γ-IFN transduced endothelial cells. Expression level of platelet-derived growth factor (PDGF), which is a smooth muscle cell growth factor normally produced by endothelial cells, was also measured to determine if decreased PDGF secretion by the γ-IFN transduced endothelial cells accounted for the smooth muscle cell inhibition. New media was placed on the cells after washing in PBS. The conditioned media was then collected after 24, 48, 72 hours in culture. Human γ-IFN levels were measured using an ELISA kit (sensitivity<5 pg/ml) purchased from Endogen. PDGF levels were measured using the R & D Systems ELISA kit (sensitivity 8.4 pg/ml for human PDGF; cross-reactivity 10% for PDGF-AA and 2% for PDGF-BB). A standard curve using recombinant protein was performed with each experiment to determine the amount of cytokine (γ-IFN or PDGF AB protein) in the conditioned media.

Major Histocompatibility Complex (MHC) expression was also measured by flow cytometry, as the presence of γ-IFN has been shown to induce MHC class II expression in endothelial cells, which normally express only MHC class I antigens.

Expression of γ-IFN, PDGF-A chain, PDGF-B chain, and glyceraldehyde 3-phosphate dehydrogenase (G3PDH) mRNA was also measured by RT-PCR to determine whether the transduced DNA was successfully transcribed into mRNA. Total RNA was extracted from transduced and non-transduced endothelial cells using Trizol reagent (Gibco BRL). Reverse transcriptase was performed for 45 minutes with 2.5 u/_l avian myeloblastosi virus reverse transcriptase, 1 mM deoxynucleoside triphosphate, 2.5 _M oligo(dT), 1 u/_l RNase inhibitor, 5 mM $MgCl_2$, and 1× PCR buffer. The amplification reaction mixture contained 1.25 u/ml Taq/50 _l, 200 mM deoxynucleotide triphosphate and 1X PCR buffer. Thirty-five cycles of 1 minute at 92° C., 1 minute at 62° C., and 2 minutes at 72° C. were performed. Primer sequences used were GGCTTTTCAGCTCTGCAT (SEQ ID NO:1; 5' primer), and GGATGCTCTTCGAC-CTCG (SEQ ID NO:2; 3' primer) for γ-IFN; TGAAG-GTCGGAGTCAACGGATTTGGT (SEQ ID NO:3; 5' primer) and CATGTGGGCCATGAGGTCCACCAC (SEQ ID NO:4; 3' primer) for G3PDH (Clontech Laboratories, Palo Alto, Calif.); AGAAGTCCAGGTGAAGGTTAGAG-GAGCAT (SEQ ID NO:5; 5' primer) and CTGCTTCAC-CGAGTGCTACAATACTTGCT (SEQ ID NO:6; 3' primer) for PDGF-A chain; CTGTCCAGGTGAGAAAGATC-GAGATTGTGCGG (SEQ ID NO:7; 5' primer) and GCCGTCTTGTCATGCGTGTGCTTGAATTTCCG (SEQ ID NO:8; 3' primer) for PDGF-B chain (Clontech Laboratories, Palo Alto, Calif.). G3PDH is a constitutively expressed housekeeping gene used as a control for RNA isolation and cDNA synthesis. After amplification, PCR products were identified by electrophoresis in 1.5% agarose gel and stained with ethidium bromide.

All statistical values are expressed as mean _SEM. Differences between groups were determined by analysis of variance (ANOVA) for multiple comparisons using the Instat™ statistical program. The Dunnett Multiple Comparisons test was used in determining significance at P values<0.05.

Data collected from ELISA analysis illustrate that transformation of endothelial cells was successful and caused the production and secretion of functional recombinant γ-IFN by the transformed endothelial cells. The functionality of recombinantly-expressed γ-IFN was determined by screening with ELISA for the presence of MHC class II antigens, as the presence of functional γ-IFN has been demonstrated to cause MHC class II expression in smooth muscle cells and endothelial cells, which normally only express MHC class I antigens. Data from this γ-IFN-mediated induction of MHC class II antigen expression are displayed in the following table.

TABLE 1

| Treatment | Percent Positive Cells (median Fluorescence) | |
|---|---|---|
| | MHC I | MHC II |
| Control cells | 94 (136) | <1 |
| β-gal tranduced cells | 96 (262) | <1 |
| γ-IFN transduced cells | 95 (1395) | 94 (302) |

This table contains data collected from human iliac artery endothelial cells that were transduced with γ-IFN or β-gal retroviral vectors and selected with G418. After two weeks, the endothelial cells were trypsinized and MHC class I and II expression was quantified by flow cytometry. MHC expression was also quantified on nontransduced control endothelial cells. Control and β-gal transduced endothelial cells showed MHC class I expression but not MHC class II expression, whereas endothelial cells transduced with γ-IFN showed MHC class II expression in addition to a level of MHC class I expression similar to both control and β-gal transduced cells. This demonstrates that transformation of endothelial cells was successful.

The data displayed in the following table demonstrate that cells transformed with the γ-IFN vector stably express and secrete a functional γ-IFN gene product in pharmacologically-active concentrations.

TABLE 2

| | Percent Positive Cells | |
|---|---|---|
| Treatment Groups | MHC I | MHC II |
| Complete Media | 82 | 0 |
| Complete Media + γ-IFN 5 u/ml | 94 | 0 |
| Complete Media + γ-IFN 50 u/ml | 97 | 0 |
| Complete Media + γ-IFN 250 u/ml | 96 | 87 |
| Non-transduced EC conditioned media | 90 | 0 |
| β-gal transduced EC conditioned media | 88 | 0 |
| γ-IFN transduced EC conditioned media | 92 | 79 |

This table contains data collected from human iliac artery smooth muscle cells that were treated with complete media or conditioned media from control, β-gal, and γ-IFN transduced endothelial cells. Media was changed every 48 hours. Smooth muscle cells were trypsinized and MHC class I and II surface expression quantified by flow cytometry. Smooth muscle cells either in the presence of exogenous γ-IFN or conditioned media from γ-IFN transduced endothelial cells both showed MHC class I and II expression, whereas endothelial cells either in the absence of exogenous γ-IFN or in the presence of conditioned media taken from endothelial cell cultures either transduced with β-gal or non-transduced cultures showed only MHC class I expression. These results demonstrate that γ-IFN-transformed cells express and secrete functional γ-IFN protein in pharmacologically-active concentrations.

Figure 1:
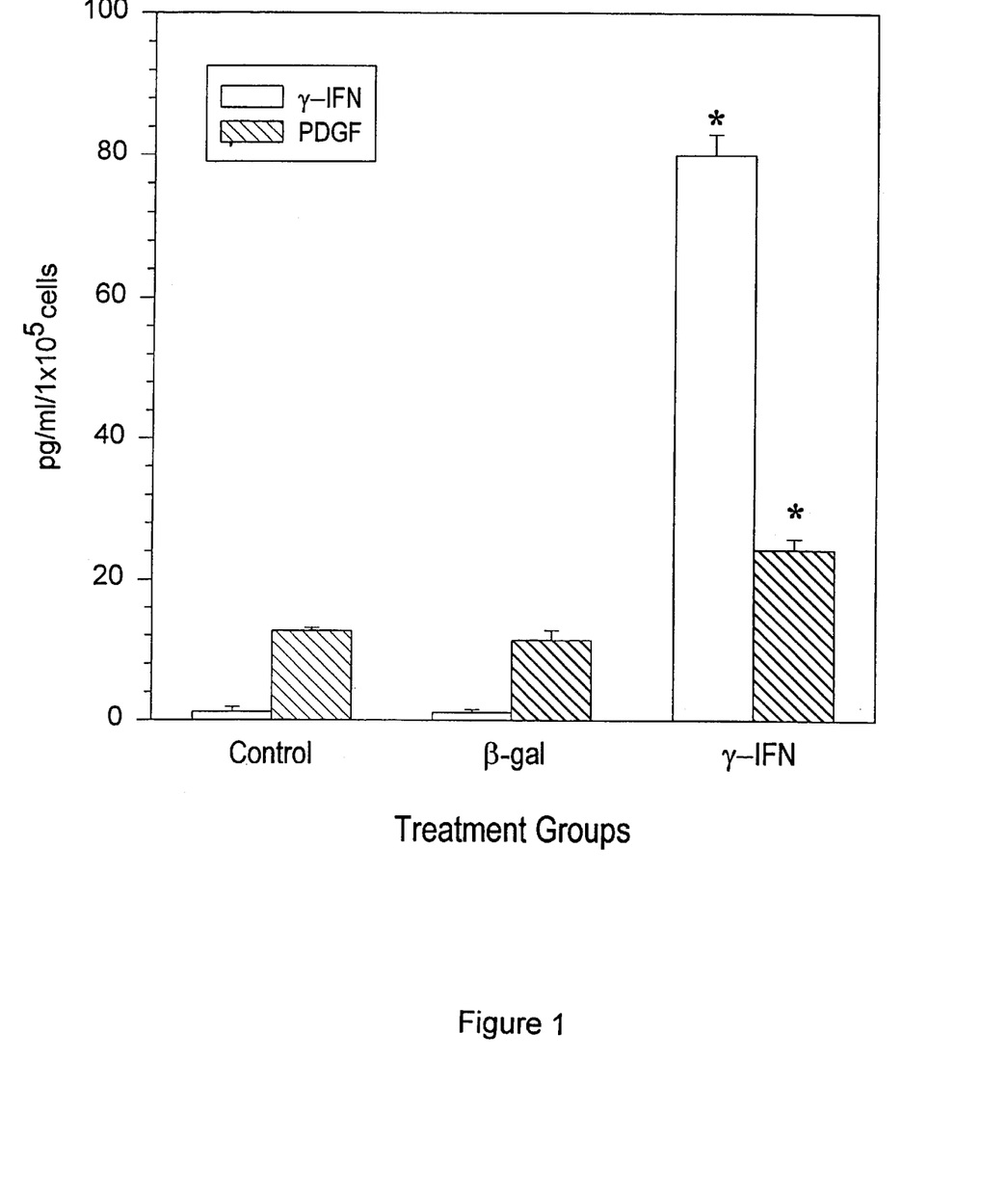

Referring to the figures, wherein like parts are designated throughout with like numerals and symbols, FIG. 1 illustrates the secreted level of expression of both γ-IFN and PDGF in conditioned media from control, β-gal transduced, and γ-IFN transduced endothelial cell cultures as measured by ELISA. Only conditioned media from γ-IFN transduced cells contained the γ-IFN protein, demonstrating that transduction with the γ-IFN vector construct causes expression of an immunohistochemically-recognizable form of γ-IFN. PDGF protein was found in the conditioned media from all endothelial cells and was significantly increased in the conditioned media from γ-IFN transduced cells. The levels of expression of PDGF-A and PDGF-B chain mRNA and PDGF-AB protein in transduced cells were determined because the inventors suspected that changes in PDGF-mediated induction of smooth muscle cell proliferation were responsible for the inhibitory effect of γ-IFN. Surprisingly, as the data in this figure shows, this was not the case. Smooth muscle cells in co-culture with γ-IFN transduced endothelial cells were exposed to increased, rather than decreased, amounts of PDGF protein. Thus, the mechanism of action of γ-IFN in inhibiting smooth muscle cell proliferation is unknown to date, and the inventors currently postulate that γ-IFN may act indirectly via other cytokines to inhibit smooth muscle cell growth.

Figure 2:
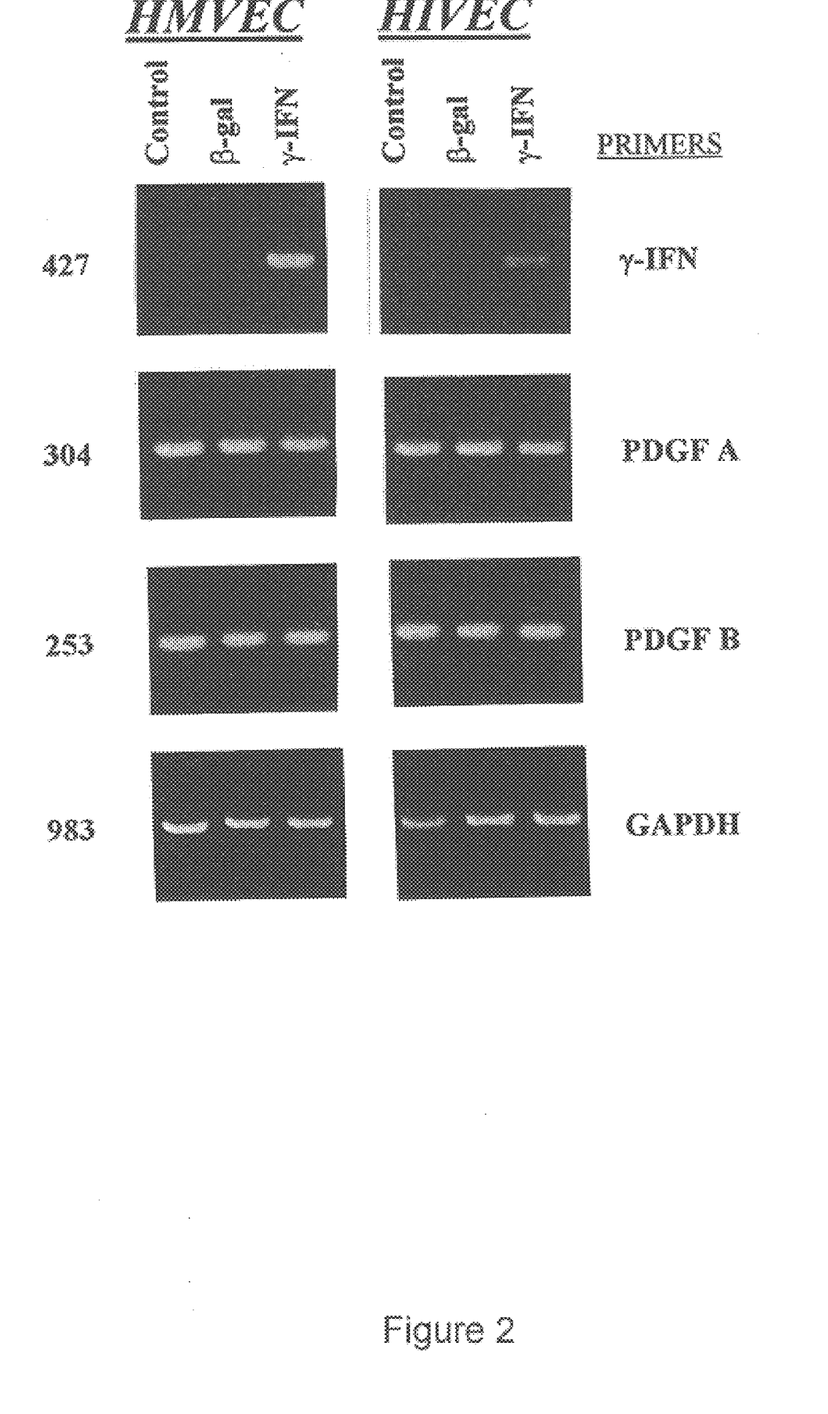
FIG. 2 is a picture of data collected from electrophoretic analysis of DNA fragments obtained from RT-PCR analysis of RNA that was isolated from control, β-gal transduced, and γ-IFN transduced human microvessel endothelial cells (HMVEC) and human iliac vein endothelial cells (HIVEC). The predicted amplification products were 427 bp for γ-IFN, 304 bp for PDGF-A chain, 253 bp for PDGF-B chain, and 983 bp for glyceraldehyde 3-phosphate dehydrogenase (G3PDH), which was utilized as a positive control.

FIG. 2 illustrates that γ-IFN mRNA is stably expressed by γ-IFN-transduced endothelial cells. Total mRNA was collected from transduced human microvessel endothelial cells (HMVEC) and human iliac artery endothelial cells (HIVEC), RT-PCR was utilized to obtain cDNA copies of γ-IFN, PDGF-A chain, PDGF-B chain, and G3PDH mRNA, if present, and then these cDNA fragments were resolved electrophoretically. Both endothelial cell types exhibited similar results. All cells expressed PDGF-A chain, PDGF-B chain, and G3PDH mRNA. Only γ-IFN transduced endothelial cells expressed γ-IFN mRNA, demonstrating that the transformation of endothelial cells with the γ-IFN vector construct causes the stabile transcription of γ-IFN mRNA.

This example, and its associated figures, has demonstrated that transformation of endothelial cells with a vector containing a gene encoding γ-IFN allows the stabile expression and secretion of functional γ-IFN protein by those transformed endothelial cells.

EXAMPLE II

Smooth Muscle Cell-Endothelial Cell Co-Culture Experiments

To determine the effect of the presence of endothelial cells expressing γ-IFN on the rate of proliferation of smooth muscle cells, equal numbers of control and transduced endothelial cells, obtained by the same procedures as described in Example I, were plated at 85% confluence on tissue culture dishes (Corning) treated with 1% gelatin. Equal numbers of smooth muscle cells were plated at 10% confluence on cell culture inserts (Minicel™-HA 0.45 _m pore size; 30 mm diameter; Millipore) and placed in culture above the endothelial cell monolayer in 100 mm tissue culture dishes or six well plates. Media was changed every two days. After 4, 6, and 8 days in co-culture, the smooth muscle cell plate insert was removed, the cells trypsinized, and the cell number counted using a Coulter Counter.

Figure 3:
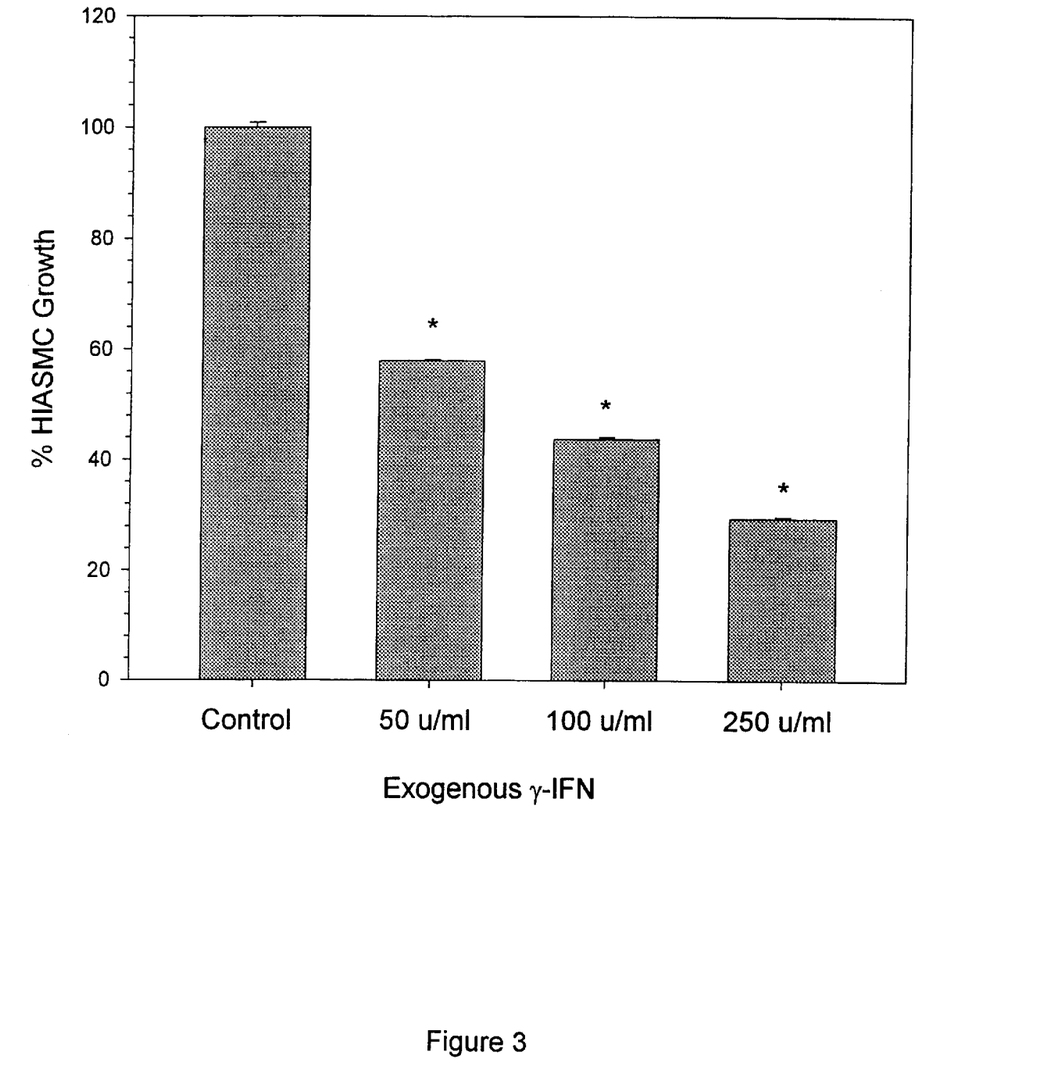
FIG. 3 is a bar graph-representation of data collected from human smooth muscle cells that were treated with exogenous human γ-IFN at 50 u/ml, 100 u/ml, and 250 u/ml. Media was replaced every 2 days and the interferon replenished. Smooth muscle cells were plated in triplicate and counted after 10 days in co-culture. Results of 5 separate experiments are pooled. A * denotes statistical significance from control at P<0.05.

Referring to the figures, wherein like parts are designated throughout with like numerals and symbols, FIG. 3 illustrates that the presence of exogenous γ-IFN inhibits the proliferation of exponentially-replicating human iliac artery smooth muscle cells (HIASMC). Statistically significant inhibition of smooth muscle cell proliferation was achieved upon treatment of those cells with 50, 100, and 250 mM exogenous human recombinant γ-IFN. Thus, the presence of γ-IFN is sufficient to inhibit smooth muscle cell proliferation.

Figure 4:
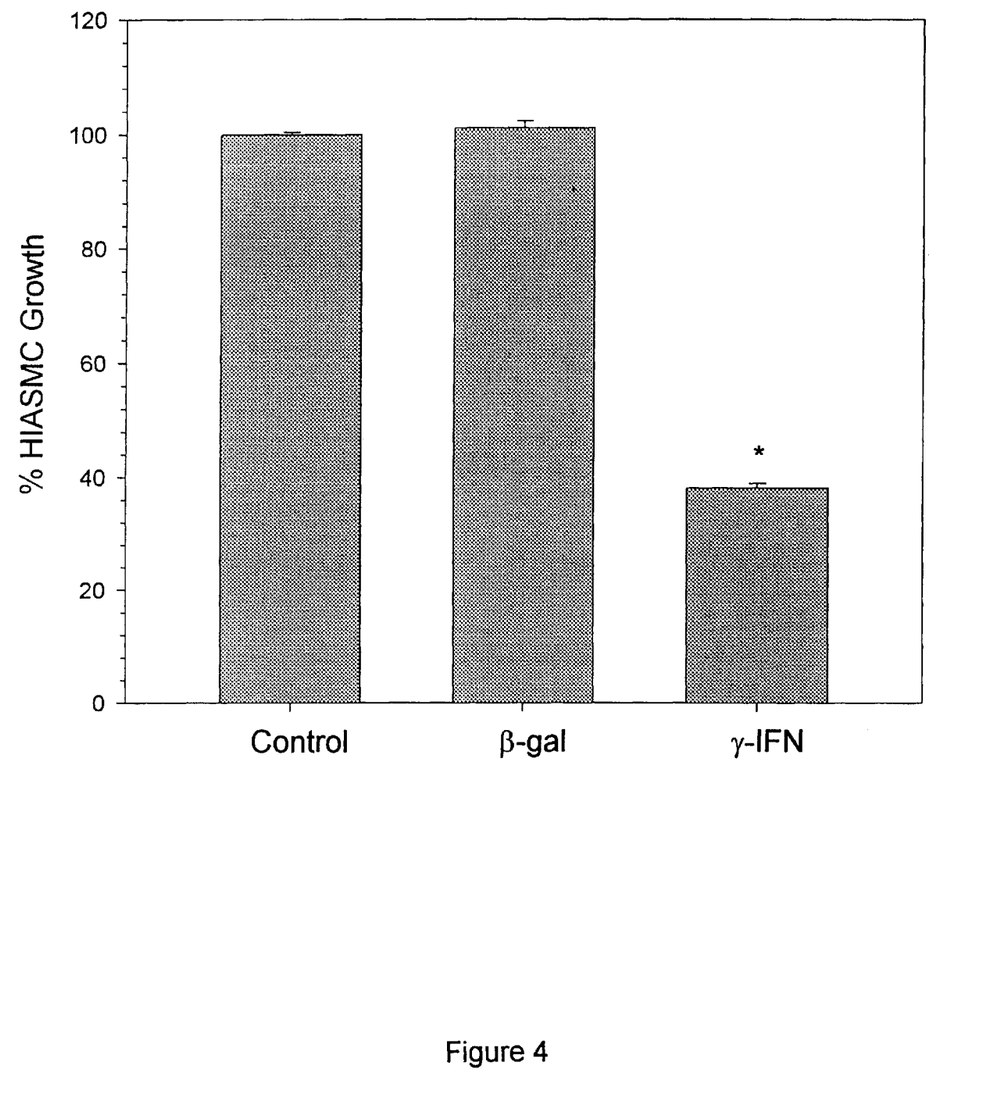
FIG. 4 and is a bar graph-representation of data collected from human iliac artery smooth muscle cells (HIASMC) that were plated in triplicate in co-culture above monolayers of control, β-gal transduced, or γ-IFN transduced human iliac artery endothelial cells. Smooth muscle cells were counted after 10 days in co-culture. Experiments were performed using endothelial cells isolated form iliac artery, vein, and microvessels, with similar results on at least three separate determinations. Results from a representative experiment are graphed. A * denotes statistical significance at P<0.05 compared nontransduced endothelial cells.

FIG. 4 illustrates that human recombinant γ-IFN expressed and secreted by endothelial cells transduced with the γ-IFN vector construct was also sufficient to inhibit smooth muscle cell proliferation. When exponentially-replicating human iliac artery smooth muscle cells (HIASMC) were plated on a monolayer of γ-IFN-transduced endothelial cells, a statistically significant inhibition of smooth muscle cell growth was observed, whereas no inhibition of smooth muscle cell proliferation was observed for nontransduced or β-gal transduced endothelial cells. This result demonstrates that the presence of endothelial cells expressing and secreting human recombinant γ-IFN is sufficient to inhibit smooth muscle cell proliferation.

While the embodiments shown in the figures and examples feature the specific structure herein described, the invention can obviously take other structures with equivalent functionality and utility. In fact, any structure or design for any of the components that retains the functional characteristics described above provides an acceptable apparatus to practice the invention. Various changes in the details, steps, and materials that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

We claim:

1. A method for inhibiting smooth muscle cell proliferation in a human vascular implant, comprising the following steps:
   (a) harvesting a patient's microvascular endothelial cells;
   (b) genetically modifying said patient's microvascular endothelial cells to cause expression and secretion of gamma-interferon for inhibiting arterial or venous smooth muscle cell proliferation;
   (c) transplanting said genetically modified microvascular endothelial cells onto at least one surface of graft material and producing an implant from the resulting transplanted graft material for implantation into a human; and
   (d) implanting said implant into an artery or vein of the patient such that said genetically modified microvascular endothelial cells inhibit muscle cell proliferation.

2. The method of claim 1, wherein said graft material in step (c) comprises an autologous vascular implant.

3. The method of claim 1, wherein said graft material in step (c) comprises a synthetic vascular implant.

4. The method of claim 1, wherein said microvascular endothelial cells are further genetically modified in step (b) to express and secrete at least one other medicinal agent in addition to gamma-interferon.

5. The method of claim 1, wherein said microvascular endothelial cells are further genetically modified in step (b) to express and secrete at least one therapeutic agent for the inhibition of thrombosis.

6. The method of claim 1, wherein the implantation of said implant is part of a therapeutic treatment for at least one form of arteriosclerosis.

7. The method of claim 1, wherein the form of arteriosclerosis is atherosclerosis.

8. The method of claim 1, wherein the implantation of said implant is part of a therapeutic treatment for at least one form of organ failure.

9. The method of claim 8, wherein said organ is a heart.

* * * * *